United States Patent
Hall

(10) Patent No.: US 6,730,129 B1
(45) Date of Patent: May 4, 2004

(54) IMPLANT FOR APPLICATION IN BONE, METHOD FOR PRODUCING SUCH AN IMPLANT, AND USE OF SUCH AN IMPLANT

(75) Inventor: Jan Hall, Göteborg (SE)

(73) Assignee: Nobel Biocare AB (SE)

( * ) Notice: Subject to any disclaimer, the term of this patent is extended or adjusted under 35 U.S.C. 154(b) by 0 days.

(21) Appl. No.: 09/980,065

(22) PCT Filed: May 19, 2000

(86) PCT No.: PCT/SE00/01022

§ 371 (c)(1),
(2), (4) Date: Feb. 28, 2002

(87) PCT Pub. No.: WO00/72775

PCT Pub. Date: Dec. 7, 2000

(30) Foreign Application Priority Data

May 31, 1999 (SE) .............................................. 9901973

(51) Int. Cl.[7] ................................................ A61L 27/00
(52) U.S. Cl. .................................. 623/23.57; 623/23.6
(58) Field of Search ....................................... 623/23.57

Primary Examiner—Cary E. O'Connor
Assistant Examiner—Candice C. Melson
(74) Attorney, Agent, or Firm—Connolly, Bove, Lodge & Hutz LLP

(57) ABSTRACT

An implant for application in bone, especially jaw bone, is provided. The implant includes a unit that can be applied in the bone, and which is made of a biocompatible material such as titanium. The unit is provided with one or more coatings including calcium phosphate and a bone-growth-stimulating substance that initiates and/or stimulates bone growth. The coating is applied at least to surface parts of the unit cooperating with the bone. A method of producing the implant is also provided.

25 Claims, 4 Drawing Sheets

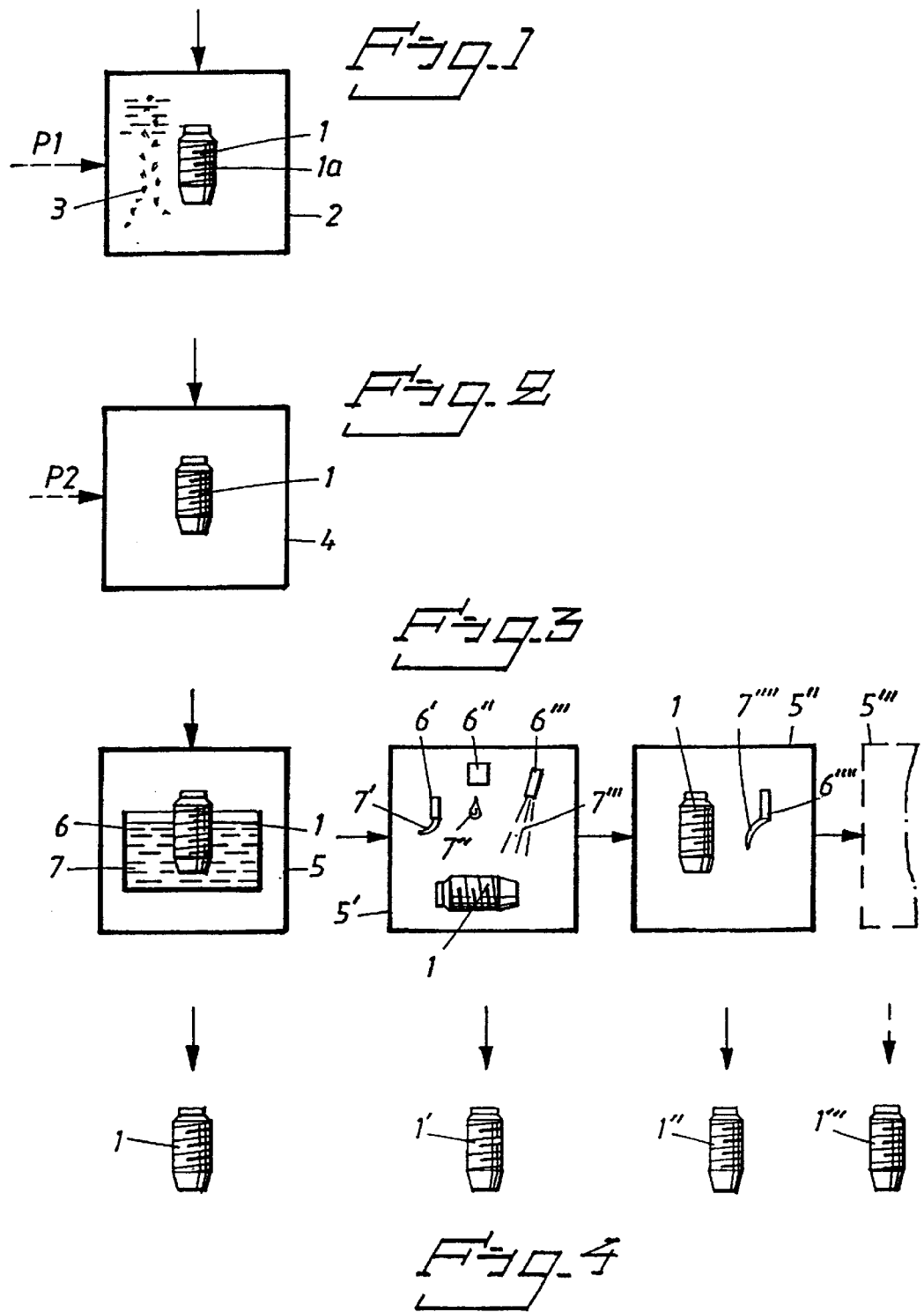

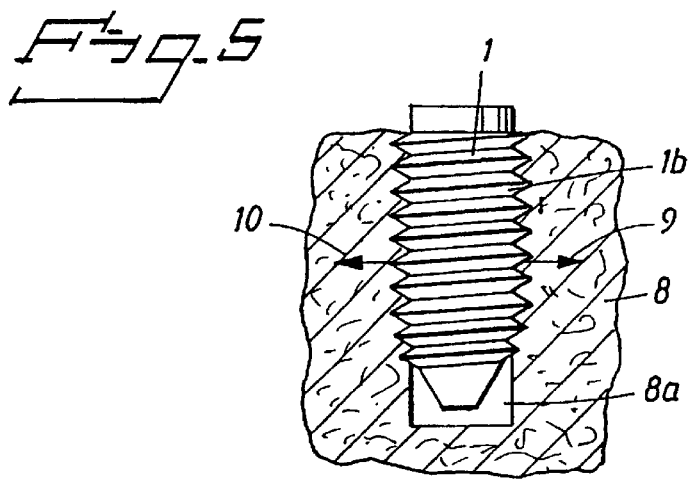
Fig. 5
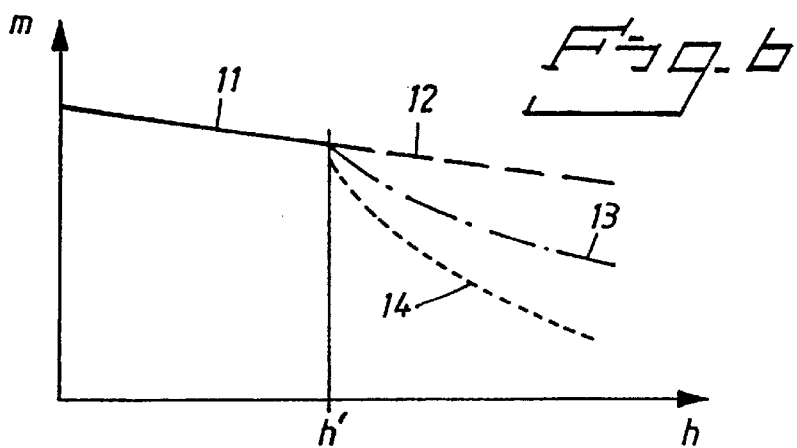
Fig. 6
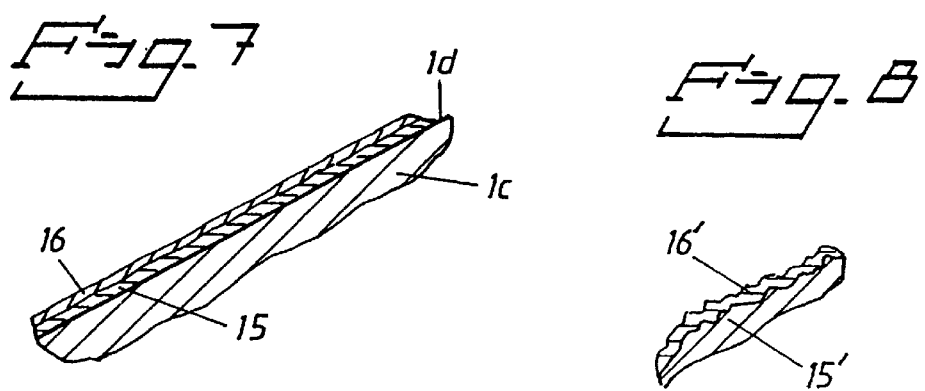
Fig. 7
Fig. 8

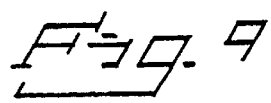
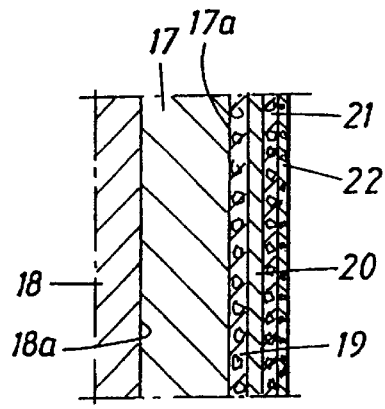
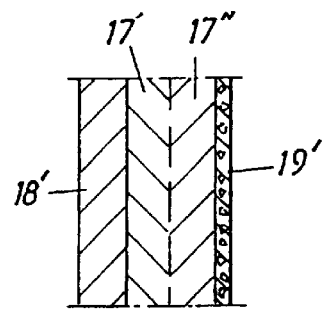
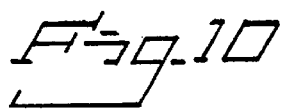
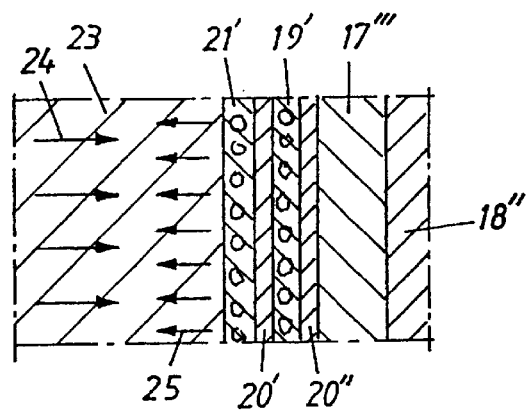
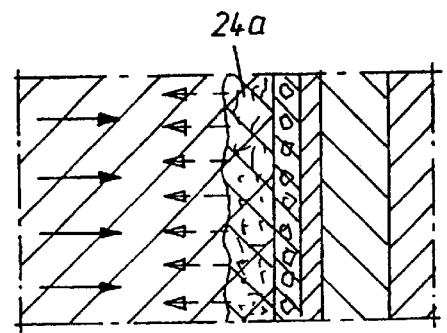
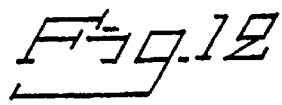
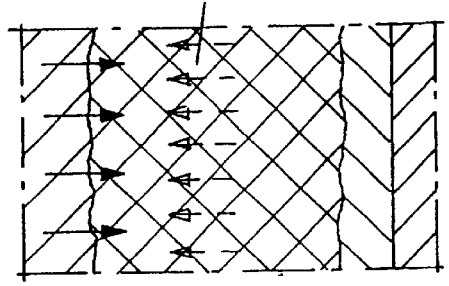

IMPLANT FOR APPLICATION IN BONE, METHOD FOR PRODUCING SUCH AN IMPLANT, AND USE OF SUCH AN IMPLANT

TECHNICAL FIELD

The present invention relates to an implant for application in bone, for example the jaw bone, primarily of the human body. The implant comprises a unit which can be applied in the bone in question and which is made of biocompatible material, preferably titanium. At least on its surface parts cooperating with the bone, the unit is provided with a coating (or coatings) as will be described below. The invention also relates to a method for producing such an implant and to the use of such an implant.

PRIOR ART

It is already known to coat implants with films or layers on those parts which are directed towards the bone in question, for example the jaw bone. The coating is intended to initiate and stimulate bone growth where the implant has been implanted or screwed into place. It is known to use hydroxyapatite or HA in the coating. The said HA can be produced by various methods, of which one advantageous method has been found to be a method called RF sputtering, with subsequent heat treatment. It is known to use calcium phosphate compounds to achieve different release times during which the agent migrates from the layer to the surrounding bone material/jaw bone material, using different degrees of crystallization. The higher the degree of crystallization, the longer the release time, and vice versa.

Reference may be made to WO 98/48862 from the same Applicant as in the present case. The said publication gives examples of methods for applying layers of this type, and layer structures which are applicable in the present invention.

Reference may be made in purely general terms to WO 88/08460 and WO 94/25637. Reference is also made to the publications "Biomaterials, Volume 17, No. 4, 1996, K. Van Dijk et al., Influence of annealing temperature on RF magnetron sputtered calcium phosphate coatings, page 405 to page 410" and "Journal of Biomedical Materials Research, Volume 28, 1994, J. G. C. Wolke et al., Study of the surface characteristics of magnetron-sputter calcium phosphate coatings, page 1477 to page 1484" and "Phosphorus Research Bulletin, Volume 6, 1996, Kimihiro Yamashita et al., Bone-Like Apatite Coating of Alumina and Zirconia by RF-Magnetron Sputtering, page 123 to page 126".

In connection with titanium implants, it is also known to arrange thick, porous titanium oxide layers which are used as depots for, inter alia, bone-growth-stimulating agents/substances (TS). In this connection, reference may be made to Swedish Patent Application No. 99 01971-3 filed on the same day and by the same Applicant, and which starts from the known arrangements according to the publications "Journal of Biomedical Materials Research, by Dann et al., Gentamicin sulfate attachment and release from anodized TI-6A1-4V orthopedic materials, Vol. 27, 895–900 (1993)" and "Journal of Biomedical Materials Research, by Hitoshi Ishizawa and Makoto Ogino, Formation and characterization of anodic titanium oxide films containing Ca and P, Vol. 29, 65–72 (1995)".

Reference is made in purely general terms to U.S. Pat. Nos. 4,330,891 and 5,354,390.

Technical Problem

At the present time, considerable efforts are being made to further develop and refine the implants, methods and uses in question here. Particularly in the case of a bone/jaw bone in which it is not entirely certain that the implant will incorporate in the bone, it is preferable to be able to call upon and use all the possibilities at present available in the areas in question, inter alia the dental area. The invention aims to solve this problem, among others.

There is a need to be able to control more exactly the release times for the transfer of the agents/substances from the implant layer to the surrounding bone tissue. Thus, for example, it may be necessary to achieve a better controlled release function during a defined or optimum time for the agents or the substances. The invention solves this problem too.

In certain cases, it is preferable for the implant surface cooperating with the bone structure to still have the prescribed degree of fineness even after the coating or coatings have been applied, in order, in certain implant cases, to be able to maintain relatively small tightening forces/screwing forces, for example for a tooth implant in a hole in the jaw bone. The invention solves this problem too.

Using a relatively coarse porosity can increase the tightening force considerably, which may be advantageous in certain cases but which should be avoided in other cases, especially in connection with hard bones. It may be noted here that improved healing processes in soft bones are needed. The invention solves this problem too.

It is also preferable to be able to use proven methods for producing the relevant type of implant despite the fact that the implant has better properties from the medical point of view. The invention solves this problem too.

It is often necessary to be able to accelerate the healing time for an implant. This can be controlled by suitable choice of coating or coatings. There are also problems in being able to correctly balance the initial bone growth stimulation and the long-term maintenance of the established bone growth. If bone growth is too rapid, this may give rise to bone fractures and other complications in bone growth. A long-term stimulation or the maintenance of bone growth are important for an implant which is to function for a long time or for many years without the implant needing to be changed. The invention solves this problem too.

In accordance with the invention, a bone-growth-stimulating substance or agent, here called TS, is to be used. Examples which may be mentioned are those substances belonging to the superfamily TGF-$\beta$, for example BMP (Bone Morphogenetic Proteins). There may be problems in preventing the said rapid release of the TS in question. It is also preferable to be able to obtain a functionally reliable support for TS upon application to an implant surface which from the outset is amorphous or heat-treated and partially crystalline. The invention solves this problem too.

There is also a need to have access to a wider range and choice of implant types which will be able to satisfy different applications on the market, cf. implants for soft bone and hard bone, etc. The invention solves this problem too.

Solution

The feature which can principally be regarded as characterizing an implant according to the invention is that the coating or coatings comprise a CaP coating with added TS. (CaP=calcium phosphate, and TS=growth-stimulating substance).

In embodiments of the inventive concept, the time for the said agent in the said coating or coatings to be released to the surrounding bone or tissue is chosen by setting the release time for CaP and the release time for TS in relation to each other. The release time for CaP is chosen with the aid of the degree of crystallization in CaP. The total release time can be chosen within the range from a few days to several months. In one embodiment, TS is applied on top of CaP. In one embodiment, the CaP coating can have a thickness in the range of between a few angstroms and 10 μm. In another illustrative embodiment, values in the range of between 0.1 μm and 20 μm can be used. All those areas of the said unit which cooperate with or are facing the bone material are preferably coated with the coating or layer in question. Each TS layer can have a thickness in the range of between a few angstroms and 1 μm.

In one embodiment, the coating or coatings comprise one or more layers of calcium phosphate compounds and one or more layers of bone-growth-stimulating substance. Agents of the release-retarding type, for example hyaluronic acid, can be interleaved with the said layers. In a further illustrative embodiment, one or more layers of CaP can have a high degree of crystallization, for example 75–100%, which means that the layer or layers have the principal role of functioning as supports for the layer or layers of TS and possibly the release-retarding agent or agents. In a further embodiment, one or more layers of CaP can have a low or medium-high degree of crystallization, for example a degree of crystallization of between slightly over 0% and 75%, which means that the layer or layers exert a support function for TS, and possibly layers of release-retarding agents are included in the bone-growth-stimulating function. The layer or layers of CaP are preferably applied nearest to or on the actual surfaces of the implant. One or more layers of TS can be applied in turn on the last-mentioned layer or on the outer of the last-mentioned layers. In the case with two or more layers of TS, layers or agents with a release-retarding function are arranged between or outside the TS layers. At least the layer or layers of TS with possible release-retarding agent can be released with components occurring naturally in the bone and/or the tissue. The said layers and possible release-retarding agents are arranged or chosen to generate bone formation around the implant, without risk of excessively rapid bone build-up and bone fracture tendencies or other complications in the bone. The said layers and possible release-retarding agents can also be arranged to effect an initially optimum bone structure around the implant in combination with long-term (over several months) bone growth or bone-growth-stimulating function. In one embodiment, one or more CaP layers consist of hydroxyapatite or HA, and one or more layers of the bone-growth-stimulating substance consist of BMP. The release-retarding agent can have a thickness of about 0.1–1.0 μm.

A method according to the invention can principally be regarded as being characterized by the fact that the said parts of the unit or the whole unit are/is coated with CaP which can be given a defined degree of crystallization by heat treatment, and TS.

CaP is preferably first applied and heat-treated, after which TS is added, for example by means of the unit, or its relevant parts to be provided with coating, being dipped in a bath of TS. Alternatively, TS can be dropped or painted onto the implant.

In a preferred embodiment, in the case where there are several TS layers, the first layer is obtained by immersing in or dropping on or painting on a TS solution with a chosen concentration. The second layer is obtained, after drying of the first layer, by dropping on or painting on of a TS solution with the chosen concentration or a second concentration which differs from the first concentration. A possible third layer is obtained, after drying of the second layer, by dropping on or painting on a TS solution with a concentration which is the same as or differs from the previously mentioned concentrations, etc. Release-retarding agents can be applied, for example by painting, on the respective dried layer. The CaP layer can be applied by so-called sputtering of CaP substance onto one or more implant surfaces which can be amorphous or heat-treated and thus crystalline. The CaP layer can be made with depressions which facilitate the holding of the outlying TS layer. Such an implant with layers of CaP and outer-lying TS layers is applied in a threaded hole in the jaw bone or equivalent in one proposed embodiment. Application methods for TS other than those mentioned can be used, for example spraying. A layer with a very high concentration of BMP can also be used.

A use, according to the invention, of the implant of the type in question is characterized essentially in that CaP and TS are used in the said coating or coatings.

Advantages

The invention makes two-fold use of substances which are known per se, which have bone-growth-stimulating properties and which at least in part are already naturally present in the human body. The use of porous oxide layers in the actual implant material as a depot for growth-stimulating substance or substances has forced the skilled person away from proposals in accordance with the present invention, principally on account of the fact that in certain cases the tightening force for the implant in bone provided with holes has had to be increased. This is not in itself a disadvantage if the total range which is to satisfy different requirements on the market is considered. The release times can, according to the invention, be chosen with great precision. The TS applied on top of the CaP coating often has greater volatility than CaP. In this way, TS can provide the surrounding jaw bone with a bone-growth-stimulating function in an initial stage, which function is gradually overtaken by the CaP coating. In one illustrative embodiment, one and the same implant serves two tissue sites located at a distance from each other.

DESCRIPTION OF THE FIGURES

A presently proposed embodiment of an arrangement, method and use according to the invention will be described below with reference to the attached drawings, in which:

FIGS. 1–4 show different stages in coating an implant with CaP layers and TS layers, FIG. 5 shows, in a vertical view and in cross section, and enlarged in relation to FIGS. 1–4, an actual implant applied in a hole made in the jaw bone, FIG. 6 shows, in graph form, release functions for the CaP and TS combination in the jaw bone, FIG. 7 shows, in a vertical view and in cross section, and enlarged in relation to FIG. 5, the CaP and TS layers applied to the surface part in question, FIG. 8 shows, in a vertical view and in cross section, and enlarged in relation to FIG. 7, the incorporation of the TS with the crystal structure of the CaP layer, FIGS. 9 and 9a show, in vertical views and in cross sections, and on an enlarged scale, the CaP and TS layers applied as multi-layers, FIGS. 10 to 12 show, in vertical sections and on an enlarged scale, the release function for multi-layers in tissue or jaw bone in the human body.

DETAILED EMBODIMENT

Figure 13:
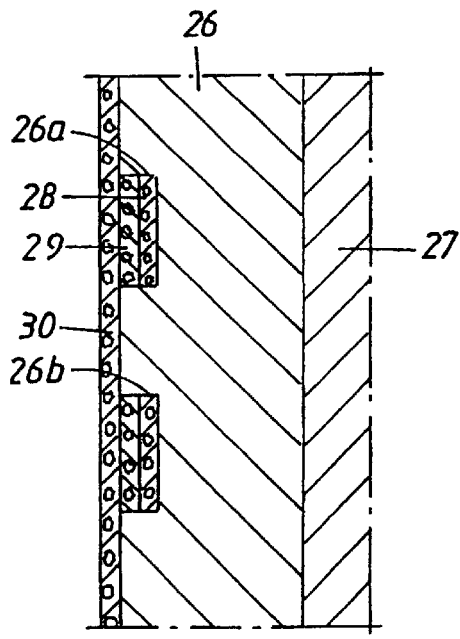
FIG. 13 shows, in vertical section and on an enlarged scale, an alternative embodiment with multi-layers.

A unit in the form of an implant is shown by 1 in FIG. 1. The surface parts 1a of the implant are to be completely or partially provided with a film-like or layered coating (or coatings). A first coating is applied in a known manner in a chamber 2, the coating being applied by so-called RF sputtering. Reference is made here to the publication WO 98/48862 mentioned in the introduction. In the chamber 2, one or more calcium phosphate compounds 3 are applied to the surface or surface parts of the unit.

After application of the actual coating, the unit 1 (its surface parts 1a) is subjected to heat treatment, which according to FIG. 2 can take place in a chamber or oven 4. Temperatures (e.g. 600° C.) and times for treatment in saturated water vapour can be chosen according to the said publication. The object of the heat treatment is to completely or partially crystallize the coating added in the chamber 2, which can be chosen with a thickness of the order mentioned above, preferably in the range of 0.1 $\mu$m to 10 $\mu$m.

In the present example, the degree of crystallization is estimated in percentages, with a degree of crystallization of 0% relating to an X-ray-amorphous surface whose thickness is at most about 50 nm.

After the treatment in the oven 4 has been carried out, the unit 1 is transferred to a station 5 according to FIG. 3. The station comprises a container 6 with TS 7, for example BMP, in which the unit or its surface parts is/are dipped for a time which is chosen as a function of TS type, release function, drying time and/or other parameter (examples of suitable times can be between 30 and 60 minutes). By means of the said immersion, TS is applied on top of the crystallized CaP layer and can at least partially by drawn by suction into the crystal structure. In alternative embodiments and methods of application, TS can be applied additionally or alternatively in other stages in the coating application. Thus, for example, it is possible for TS to be incorporated in the stages according to FIGS. 1 and/or 2, which has been symbolically indicated by broken line arrows P1 and P2. In another embodiment of the invention, the TS layer can be applied in another way, for example by dropping or painting it on and/or spraying it on.

The station 5 can also comprise equipment for further treatment of the implant 1. Thus, further TS substance can be applied in a subsidiary station 5' in order to achieve double TS layers on the surface of the implant 1. This second method can be carried out by painting 7', dropping 7" or spraying 7'". The concentration of TS in the solution can be identical or different in the various applications. It can be applied by brush 6', nozzle 6" or spray unit 6'". The station according to FIG. 3 can comprise a further subsidiary station 5" where, by means of equipment 6"", release-retarding, visco-elastic material, for example hyaluronic acid 7"" is applied, for example by means of painting or spraying, in one or more layers on the surface(s) of the implant 1. The station according to FIG. 3 can comprise a further subsidiary station 5'", and so on, where further application of TS layers and/or release-retarding layers are applied in the same way as at subsidiary station 5".

FIG. 4 shows the finished unit 1. After treatment in the station according to FIG. 3, the implant can thus be provided with various layers, which has been symbolized by 1 which has a single layer of TS, 1' which has a double layer of TS, 1" which has double layers of TS and release-retarding layers, 1'" which has further layers, etc. Alternatively, the CaP and TS layers can be applied using a different station arrangement, and reference may be made here to the possibility of plasma-sprayable Cap including TS.

According to FIG. 5, the unit can consist of a screw implant provided with thread or threads and intended to be screwed into a jaw bone 8 which has been provided with a hole 8a in which to screw the implant. The invention can also be used on other types of implants. After application in the bone, TS and CaP are released into the bone structure in accordance with the description below. This release has been symbolized by arrows 9 and 10. In the illustrative embodiment, the unit/implant is made of titanium, i.e. biocompatible material.

FIG. 6 shows possible examples of release functions for TS and CaP. In the diagram, the horizontal axis represents the time h and the vertical represents the quantity m, the curves thus representing the specified quantity per unit of time. The curve 11 illustrates a desired release function from implants with multi-layers of TS and release-retarding agent as above. The layers in question can be intended to be released at the time h". Depending on the degree of crystallization in the CaP layer(s), the said layer or layers can assume bone growth stimulation or maintain bone growth. The curve 12 represents CaP layers with amorphous or low-crystalline character which continues release of bone stimulation function to a the bone. The curve 13 represents a medium-high degree of crystallization, for example 25–75%. The curve 14 represents a high degree of crystallization, meaning 75–100%. At 100% crystallization, the layer functions as a support of preferably surface-bound TS. Initially high bone growth stimulation can be followed by long-term stimulation and maintenance of bone growth can thus be achieved. The breakdown or release functions are or can be related to the actual acid environment. It is desirable for the initial bone growth stimulation to be rapid so that the times for healing and prosthesis application can be reduced compared to previous times. However, the bone growth stimulation must not be too rapid since this causes collapse within the grown bone structure. The invention can solve this problem by making possible precise selection of the release times. The time h1 can be chosen, for example, to be 2–4 weeks. The long-term stimulation can be chosen to be months or years after the period of incorporation.

FIG. 7 shows on a greatly enlarged scale a part 1c of the unit 1. The part 1c in question can be part of a thread whose surface 1d is to be coated with one or more CaP layers 15 and with TS layers 16 applied on top of the latter. It should be noted here that the invention also satisfies the requirements for great surface fineness on the surface 1d (cf. said publication).

FIG. 8 shows, again on an enlarged scale, how the crystal structure 15' has to a certain extent drawn TS 16' in.

In FIG. 9, a CaP layer is indicated by 17. The layer is applied on the metal in question, for example titanium 18, on a surface 18a which can be worked with a greater or lesser degree of fineness. The layer 17 can have a degree of crystallization of 0–100%. A first layer 19 of TS is applied to the outer surface 17a of the layer 17. This is followed by a second layer 20 of release-retarding agent, on which a second layer 21 of TS is applied. A third layer 22 of TS is in turn applied on the layer 21. The layer combination shown is only one example.

According to FIG. 9a, the CaP layer according to FIG. 9 can also be divided into two or more layers 17', 17" which can be provided with identical or different degrees of crystallization. The layer 17" supports a TS layer on its outside, etc.

FIGS. 10, 11 and 12 show the time-dependent breakdown of the various layers in bone or tissue. Breakdown components in the tissue or the bone are symbolized by arrows 24. The initial bone-growth stimulation is symbolized by arrows 25, which stimulation is thus initiated by means of the outer layer 21' of TS. The titanium or equivalent has been designated by 18".

In FIG. 11, the bone growth has started and is shown by 24a. In the stage according to FIG. 11, the outer layers 21' and 20' according to FIG. 10 have completely or partially disintegrated. In the stage according to FIG. 12, the layers 19', 20" and parts of the layer 17'" have also disintegrated and resulted in bone growth 24a'.

The said components thus begin the breakdown with the outermost layer, after which breakdown proceeds successively, layer by layer, until the CaP layer is exposed and subjected to the components.

In FIG. 13, reference number 26 shows a CaP layer and reference number 27 shows the metal in the implant. The layer 26 can be provided with depressions 26a, 26b or other irregular surface structures which can accommodate TS layers 28, 29, 30 of different geometrical extents along the outer surface of the CaP layer, etc.

Figure 14:
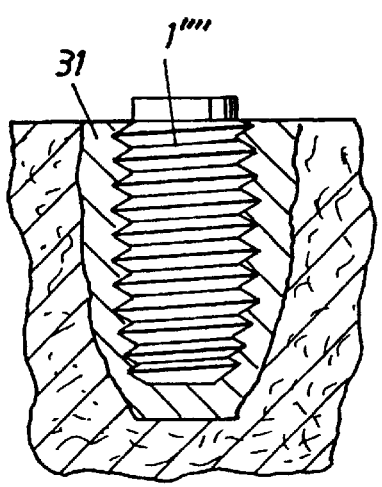
FIGS. 14 and 15 show, in vertical sections, different examples of bone formation in tissue or bone.
Figure 15:
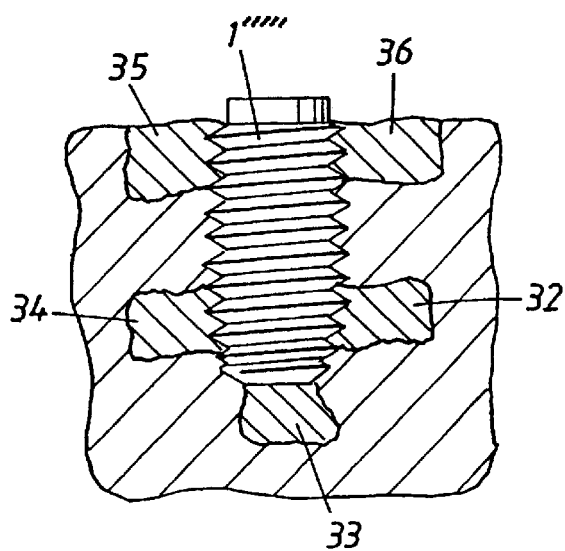

In FIGS. 14 and 15, two implants 1"" and 1"''' with different initial layer structures have initiated bone growths 31 and 32, 33, 34, 35, 36, respectively. The first bone growth 31 has a sock-shaped appearance, while the second one is more O-shaped. A characteristic feature is that the bone growth function achieves very good osteoconduction around or osteointegration within the implant or implant parts, which guarantees good incorporation in the bone structure.

The invention is not limited to the embodiment given above by way of example, and can be modified within the scope of the attached patent claims and the inventive concept.

What is claimed is:

1. An implant for application in bone, said implant comprising a unit adapted to be applied in the bone, said unit being made of biocompatible material, wherein the implant includes at least one coating of at least one calcium phosphate layer comprising at least one calcium phosphate compound, and at least one bone-growth-stimulating layer comprising a bone-growth-stimulating substance applied on the at least one calcium phosphate layer, wherein the at least one coating is provided at least on surface parts of the implant cooperating with the bone, and wherein the at least one calcium phosphate layer and the at least one bone-growth stimulating layer are arranged to effect an initial optimal bone structure around the implant in combination with long term bone growth or bone-growth or bone-growth-promoting function.

2. An implant according to claim 1, wherein the at least one calcium phosphate layer has a thickness in the range of between a few angstroms and 10 $\mu$m, and wherein the at least one bone-growth-stimulating layer has a thickness of between a few angstroms and 1 $\mu$m.

3. An implant according to claim 1, wherein all areas of said surface parts are provided with the at least one coating.

4. An implant according to claim 1, wherein the at least one calcium phosphate layer is located nearest to or on the actual surfaces of the implant, and wherein the at least one bone-growth-stimulating layer is located on the at least one calcium phosphate layer or on an outermost one of the at least one calcium phosphate layer.

5. An implant according to claim 1, wherein the at least one calcium phosphate layer has a high degree of crystallization such that the at least one calcium phosphate layer functions as a support for the at least one bone-growth-stimulating layer.

6. An implant according to claim 1, wherein the at least one bone-growth-stimulating layer comprises a plurality of bone-growth-stimulating layers, and wherein at least one layer or agent with a release-retarding function for the bone-growth-stimulating substance is interleaved with the bone-growth-stimulating layers.

7. An implant according to claim 1, wherein one or more layers among the at least one calcium phosphate layer contain hydroxyapatite or HA, and wherein one or more layers among the at least one bone-growth-stimulating layer consist of a substance belonging to the superfamily TGF-$\beta$.

8. An implant according to claim 1, wherein the at least one calcium phosphate layer has a thickness in the range of between 0.1 $\mu$m and 20 $\mu$m, and wherein the at least one bone-growth-stimulating layer has a thickness of between a few angstroms and 1 $\mu$m.

9. An implant according to claim 1, wherein the at least one calcium phosphate layer has a low or medium-high degree of crystallization such that the at least one calcium phosphate layer functions as a support for the at least one bone-growth-stimulating layer.

10. An implant according to claim 9, wherein at least one layer of a release-retarding agent is included in a bone-growth-stimulating function.

11. An implant according to claim 1, wherein one or more layers among the at least one bone-growth-stimulating layer with release-retarding agents can be released with components occurring naturally in the bone and/or tissue.

12. An implant according to claim 11, wherein the at least one calcium phosphate layer, the at least one bone-growth stimulating layer and the release-retarding agents are arranged or chosen to generate bone formation in the surrounding tissue around the implant without the risk of excessively rapid bone build-up and bone fracture tendencies.

13. An implant according to claim 1, wherein a release time for agents in said at least one coating is chosen by setting a release time for the at least one calcium phosphate compound and a release time for the bone-growth-stimulating substance in relation to each other.

14. An implant according to claim 13, wherein a release time for the at least one calcium phosphate compound is chosen with the aid of a degree of crystallization in the at least one calcium phosphate compound, wherein a higher degree of crystallization gives a longer release time, and wherein a lower degree of crystallization gives a shorter release time.

15. An implant according to claim 14, wherein the degree of crystallization in the at least one calcium phosphate compound is chosen to give a total release time of at least 2–4 weeks up to several months.

16. An implant according to claim 1, wherein the at least one coating further comprises at least one layer of release-retarding agents.

17. An implant according to claim 16, wherein the release-retarding agent is hyaluronic acid.

18. An implant according to claim 16, wherein the at least one calcium phosphate layer has a high degree of crystallization such that the at least one calcium phosphate layer functions as a support for the at least one bone-growth-stimulating layer and the release-retarding agent.

19. A method for arranging at least one coating on an implant for application in bone, wherein said implant comprises a unit of biocompatible material, wherein the coating is applied at least on surface parts of the unit cooperating with the bone, the method comprising: coating the surface parts or the whole unit with at least one calcium phosphate compound; applying at least one bone-growth-stimulating substance on the at least one calcium phosphate compound, wherein the at least one calcium phosphate compound is X-ray-amorphous or given a specific degree of crystallization; and applying a release-retarding-agent by painting on the at least one bone-growth stimulating substance.

20. A method according to claim 19, wherein the release-retarding agent is hyaluronic acid or a visco-elastic substance.

21. A method according to claim 19, wherein the calcium phosphate compound is first applied and crystallized completely or partially in at least one calcium phosphate layer and wherein the bone-growth stimulating substance is then applied in at least one bone-growth stimulating layer by immersing the unit or parts of the unit in a bath of bone-growth-stimulating substance or by dropping bone-growth-stimulating solution on the unit or parts of the unit.

22. A method according to claim 21, wherein the at least one bone-growth-stimulating layer comprises several bone-growth-stimulating layers, wherein a first bone-growth-stimulating layer is obtained by immersing in or dropping on a bone-growth-stimulating solution at a chosen concentration, wherein a second bone-growth-stimulating layer is obtained, after drying of the first bone-growth-stimulating layer, by dropping on or painting on a bone-growth-stimulating solution at said chosen concentration or a second concentration which differs from said chosen concentration, and wherein a third bone-growth-stimulating layer is obtained, after drying of the second bone-growth-stimulating layer, by dropping on or painting on a bone-growth-stimulating solution at said chosen concentration or a third concentration which differs from said chosen and/or said second concentration.

23. A method according to claim 19, wherein the at least one calcium phosphate compound is applied by sputtering of a calcium phosphate substance in at least one calcium phosphate layer on originally essentially amorphous implant surfaces and by subsequent heat treatment.

24. A method according to claim 23, further comprising applying and heat treating the at least one calcium phosphate compound such that depressions are obtained in the at least one calcium phosphate layer, wherein the depressions contribute to increasing the attachment of an outer bone-growth-stimulating layer in the at least one calcium phosphate layer, and wherein the biocompatible material comprises titanium.

25. A method for arranging at least one coating on an implant for application in bone, wherein said implant comprises a unit of biocompatible material comprising titanium, wherein the coating is applied at least on surface parts of the unit cooperating with the bone, the method comprising: coating the surface parts or the whole unit with at least one calcium phosphate compound by sputtering of a calcium phosphate substance in at least one calcium phosphate layer on originally essentially amorphous implant surfaces and by subsequently heat treating the at least one calcium phosphate compound such that depressions are obtained in the at least on calcium phosphate layer; and applying at least one bone-growth-stimulating substance on the at least one calcium phosphate compound, wherein the at least one calcium phosphate compound is X-ray-amorphous or given a specific degree of crystallization, and wherein the depressions contribute to increasing the attachment of an outer bone-growth-stimulating layer in the at least one calcium phosphate layer.

* * * * *